(12) United States Patent
Antonelli et al.

(10) Patent No.: US 9,974,554 B2
(45) Date of Patent: May 22, 2018

(54) DEVICES AND METHODS FOR REMOVAL OF CALCULUS

(71) Applicant: The Board of Regents of the University of Texas System, Austin, TX (US)

(72) Inventors: Jodi A. Antonelli, Dallas, TX (US); Heather E. Beardsley, Arlington, TX (US); Justin I. Friedlander, Philadelphia, PA (US); Jeffrey C. Gahan, Dallas, TX (US); Monica S. C. Morgan, Dallas, TX (US); Margaret S. Pearle, Dallas, TX (US); Jeffrey A. Cadeddu, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 350 days.

(21) Appl. No.: 14/844,600

(22) Filed: Sep. 3, 2015

(65) Prior Publication Data

US 2016/0066934 A1 Mar. 10, 2016

Related U.S. Application Data

(60) Provisional application No. 62/046,359, filed on Sep. 5, 2014.

(51) Int. Cl.
*A61B 17/22* (2006.01)
*A61B 17/221* (2006.01)
(Continued)

(52) U.S. Cl.
CPC ...... *A61B 17/221* (2013.01); *A61B 17/00234* (2013.01); *A61B 17/2251* (2013.01);
(Continued)

(58) Field of Classification Search
CPC .......... A61B 17/221; A61B 2017/2215; A61B 17/22031; A61B 2017/22035; A61B 17/225; A61B 17/2251; A61B 2017/00287
See application file for complete search history.

(56) References Cited

U.S. PATENT DOCUMENTS 4,590,938 A 5/1986 Segura et al.
4,625,726 A 12/1986 Duthoy
(Continued)

FOREIGN PATENT DOCUMENTS

WO WO 2013/173577 11/2013

OTHER PUBLICATIONS

Antonelli et al., "PercSac: a novel device to prevent stone migration during percutaneous lithotripsy," Presentation, American Urologic Association Annual Meeting, May 2014.
(Continued)

*Primary Examiner* — Jonathan Miles
(74) *Attorney, Agent, or Firm* — Parker Highlander PLLC

(57) ABSTRACT

Devices and methods for removal of calculus (including for example, kidney stones) are disclosed. In an embodiment, a device for removal of kidney stones includes a substantially sealable pouch that can be inserted into the kidney for capturing a kidney stone. The pouch is also designed to permit fragmentation of the kidney stone inside the pouch, while preventing kidney stone fragments from escaping from the pouch. As a result, the likelihood of dispersing stone fragments during fragmentation of a large stone is greatly lessened.

22 Claims, 4 Drawing Sheets

(51) Int. Cl.
*A61B 17/00* (2006.01)
*A61B 17/225* (2006.01)

(52) U.S. Cl.
CPC .............. *A61B 2017/00287* (2013.01); *A61B 2017/2212* (2013.01); *A61B 2017/2215* (2013.01)

(56) References Cited

U.S. PATENT DOCUMENTS

| | | | |
|---|---|---|---|
| 4,893,621 A | | 1/1990 | Heyman |
| 4,997,435 A | | 3/1991 | Demeter |
| 5,190,542 A | | 3/1993 | Nakao et al. |
| 5,190,561 A | * | 3/1993 | Graber ............. A61B 17/00234 606/114 |
| 5,341,815 A | | 8/1994 | Cofone et al. |
| 5,403,324 A | | 4/1995 | Ciervo et al. |
| 5,611,803 A | | 3/1997 | Heaven et al. |
| 5,785,677 A | * | 7/1998 | Auweiler ......... A61B 17/00234 128/850 |
| 6,264,663 B1 | | 7/2001 | Cano |
| 6,447,523 B1 | | 9/2002 | Middleman et al. |
| 7,537,601 B2 | | 5/2009 | Cano et al. |
| 7,914,540 B2 | | 3/2011 | Schwartz et al. |
| 2001/0002437 A1 | * | 5/2001 | Pagedas ........... A61B 17/00234 606/114 |
| 2003/0178030 A1 | | 9/2003 | Constantz |
| 2004/0242960 A1 | * | 12/2004 | Orban, III .............. A61B 10/04 600/106 |
| 2006/0247663 A1 | | 11/2006 | Schwartz et al. |
| 2006/0253123 A1 | * | 11/2006 | Wilk .................. A61B 17/3423 606/114 |
| 2008/0103508 A1 | * | 5/2008 | Karakurum ...... A61B 17/00234 606/127 |
| 2008/0221588 A1 | * | 9/2008 | Hollis .............. A61B 17/00234 606/114 |
| 2009/0222035 A1 | * | 9/2009 | Schneiderman ..... A61B 17/221 606/200 |
| 2009/0306683 A1 | | 12/2009 | Zwolinski et al. |
| 2010/0016792 A1 | * | 1/2010 | Hirszowicz ...... A61B 17/22031 604/96.01 |
| 2010/0152609 A1 | * | 6/2010 | Zwolinski .............. A61B 10/06 600/566 |
| 2010/0219091 A1 | * | 9/2010 | Turner ............. A61B 17/00234 206/438 |
| 2012/0203241 A1 | * | 8/2012 | Williamson, IV ..... A61B 10/06 606/114 |
| 2013/0310803 A1 | * | 11/2013 | Morsi .................. A61B 17/221 604/508 |
| 2014/0031852 A1 | | 1/2014 | Edgren et al. |
| 2014/0257362 A1 | * | 9/2014 | Eidenschink ........... A61F 2/013 606/200 |
| 2015/0133949 A1 | | 5/2015 | Cadeddu et al. |
| 2016/0066934 A1 | * | 3/2016 | Antonelli ............. A61B 17/221 606/128 |
| 2017/0252026 A1 | * | 9/2017 | Gupta .............. A61B 17/00234 |

OTHER PUBLICATIONS

Antonelli et al., "PercSac: a novel device to prevent stone fragment migration during percutaneous lithotripsy," Abstract V10-03, *Scientific Program for 31st World Congress of Endourology & SWL Program Book,* 27(Suppl 1):V10-03, Sep. 2013.

Faddegon et al.,"A novel device to prevent migration of stone fragments during percutaneous lithotripsy," Abstract MP40-04, *Scientific Program for 30th World Congress of Endourology & SWL,* 26(Suppl 1):MP40-04, Sep. 2012.

Faddegon et al.,"A novel device to prevent migration of stone fragments during percutaneous lithotripsy," Abstract 28, *27th Engineering and Urology Society Annual Meeting,* May 2012.

Friedlander et al.,"A novel device to prevent stone fragment migration during percutaneous lithotripsy," *Journal of Endourology,* 28(12):1395-1398, 2014.

PCT International Search Report and Written Opinion issued in International Application No. PCT/US2015/048266, dated Dec. 2, 2015.

\* cited by examiner

DEVICES AND METHODS FOR REMOVAL OF CALCULUS

CROSS REFERENCE TO RELATED APPLICATIONS

This application claims priority to U.S. Provisional Patent Application 62/046,359 filed Sep. 5, 2014, the contents of which are incorporated by reference herein.

BACKGROUND OF THE INVENTION

1. Field of the Invention

Exemplary embodiments of the present invention relate generally to the fields for removal of calculus from a patient. More particularly, exemplary embodiments concern containment and removal of fragments of calculus, including for example, kidney stones.

2. Description of Related Art

During a percutaneous nephrolithotomy (PCNL) procedure, a telescope is passed directly into the kidney through a small incision in the flank to remove large kidney stones from the kidney. Oftentimes, large kidney stones need to be fragmented before they can be removed, and it is important to remove all resulting fragments in order to minimize the risk of stone recurrence. Small fragments of kidney stones, however, may migrate and drift into the renal calyces or down the ureter, requiring the surgeon to insert a flexible endoscope to search the entire kidney for residual fragments, which increases operative time and, thus cost of the procedure. Occasionally, despite inspection of the kidney, fragments are missed and are detected on Computer Tomography (CT) scan only after the surgery. Removal of these residual fragments requires a second procedure in the operating room.

Devices and methods that would limit stone particle migration during active stone fragmentation could result in reduced operative time, less need for costly post-procedure CT scans and less frequent need to return to the operating room to remove missed stone fragments.

SUMMARY

Devices and methods for removal of calculus (including for example, kidney stones) are disclosed herein. Up to fifty percent of patients with residual fragments after percutaneous nephrolithotomy (PCNL) experience a stone-related event. Exemplary embodiments of the present disclosure comprise a polyethylene sack (sometimes referred to as a PercSac) that fits over the shaft of a rigid nephroscope and is deployed in the collecting system to capture a stone and contain fragments generated during PCNL. Use of exemplary embodiments can provide for efficient and complete removal of stones.

According to aspects illustrated herein, there is provided a device for removal of kidney stones that includes a substantially sealable pouch that can be inserted through an Amplatz sheath simultaneously with a rigid nephroscope to entrap stones that are too large to be extracted through the sheath. The pouch is designed to permit the surgeon to insert the nephroscope and a fragmenting device into the pouch and fragment the stone inside the pouch under direct vision. In some embodiments, stones up to 2.5 cm in diameter can be entrapped in the pouch and fragmented via the nephroscope and lithotrite, thereby preventing stone fragments from migrating down the ureter or elsewhere within the renal collecting system. As a result, the likelihood of dispersing stone fragments during fragmentation of a large stone is greatly reduced, if not completely prevented.

According to aspects illustrated herein, there is provided a method for removal of kidney stones that includes advancing the pouch into the kidney, inserting a grasper tool through a nephroscope tool port and through the opening of the pouch, grasping the stone and pulling it into the pouch. Exemplary embodiments may further comprise sealing the pouch, releasing and removing the grasper tool from the nephroscope, fragmenting the kidney stone into smaller fragments, and removing the kidney stone fragments from the pouch while maintaining the seal of the pouch Certain exemplary embodiments may comprise advancing a sealable pouch into the kidney, moving the pouch over a kidney stone to capture the kidney stone inside the pouch, closing a mouth of the pouch to seal the pouch, fragmenting the kidney stone into smaller fragments, and removing the kidney stone fragments from the pouch while maintaining the seal of the pouch.

Exemplary embodiments include a medical device for use in the removal of a calculus from a patient. The medical device may comprise: a tubular member comprising a proximal end and a distal end; and a flexible pouch coupled to the tubular member, where the flexible pouch comprises a distal end opening and a proximal end opening. The distal end opening may be oriented substantially perpendicular to the tubular member and oriented away from the proximal end of the tubular member. The device may also comprise a resilient loop extending around the distal end opening of the flexible pouch; and a first control line coupled to the resilient loop, where the first control line is configured to manipulate the resilient loop such that the distal end opening can be moved from an open position to a closed position.

The medical device of claim 1 may further comprise a clamp configured to secure the first control line in a desired position. In particular embodiments, the distal end opening may be configured to retain a particle with diameter of approximately 0.5 mm when the distal end opening is in the closed position. In certain embodiments, the distal end opening may have a diameter of less than 1.0 mm when the distal end opening is in the closed position. In specific embodiments, the distal end opening may have a diameter of less than 0.5 mm when the distal end opening is in the closed position. In particular embodiments, the resilient loop and the first control line may be formed from a single component, and in certain embodiments, the resilient loop and the first control line are formed from a nitinol wire.

In specific embodiments, the first control line: enters the proximal end of the tubular member; exits the distal end of the tubular member; extends through a channel around the distal end opening to form the resilient loop; re-enters the distal end of the tubular member; and exits the proximal end of the tubular member. In particular embodiments, the resilient loop may be biased to maintain the distal end opening in the open position. In certain embodiments, the resilient loop may be formed from a shape memory material.

In certain embodiments, the distal end opening may be between approximately 1 cm and 5 cm in diameter when the distal end opening is in the open position. In particular embodiments, the distal end opening may be between approximately 2 cm and 5 cm in diameter when the distal end opening is in the open position, and in specific embodiments may be approximately 3.5 cm in diameter when the distal end opening is in the open position.

In certain embodiments, the flexible pouch may comprise a generally cylindrical portion near the distal end opening. In particular embodiments, the flexible pouch may comprise a tapered portion coupled to the generally cylindrical portion. In specific embodiments, the flexible pouch may comprise an elongated portion coupled to the tapered portion. In certain embodiments, the elongated portion may be approximately 5-20 centimeters long, including approximately 11 cm centimeters long or approximately 17.5 cm centimeters long. In specific embodiments, the elongated portion may be approximately 60 cm centimeters long. In particular embodiments, the flexible pouch may comprise a funnel-shaped overflow portion coupled to the elongated portion.

In certain embodiments, the generally cylindrical portion and the tapered portion may be formed from a polyethylene material that is approximately 0.038 mm thick, and the elongated portion and the funnel-shaped overflow portion may be formed from a polyethylene material that is approximately 0.051 mm thick. In specific embodiments, the elongated portion may be approximately 9 mm in diameter.

In particular embodiments, the first control line may extend along the tubular member; the first control line may be coupled to the resilient loop; and the first control line may be pulled toward the distal end of the tubular member to close the distal end opening.

Certain embodiments may further comprise a second control line coupled to the resilient loop, where the first and second control lines may be configured to manipulate the resilient loop such that the distal end opening can be closed. In particular embodiments, the resilient loop may be displaced in a channel that extends around the distal end opening. In specific embodiments, the channel may be formed by folding a portion of the flexible pouch. In certain embodiments, the flexible pouch may be formed from a polyethylene material. In particular embodiments, the tubular member may be formed from a biocompatible metal. In specific embodiments, the tubular member may be formed from stainless steel.

Certain embodiments may include a medical device for use in the removal of a calculus from a patient, where the medical device comprises: a pouch formed from a flexible material; a distal end opening in the pouch; a proximal end opening in the pouch; and a tubular member coupled to the pouch. In particular embodiments, the distal end opening may be configured to move from an open position to a closed position; the distal end opening may be configured to receive the calculus in the pouch when the distal end opening is in the open position; the distal opening may be configured to retain the calculus in the pouch when the distal opening is in the closed position; and the proximal end opening may be configured to receive a medical instrument configured to fragment a calculus.

In certain embodiments, the distal end opening may be between approximately 2 cm and 5 cm in diameter when the distal end opening is in the open position, including approximately 3.5 cm in diameter when the distal end opening is in the open position.

Specific embodiments may further comprise a control line configured to move the distal end opening from the open position to the closed position, where the control line extends from the distal end opening to the proximal end opening. In certain embodiments, the control line may be coupled to a resilient loop extending around the distal end opening, and the control line and the resilient loop may be formed from a single component. In particular embodiments, the resilient loop may be biased to maintain the distal end opening in the open position, and the resilient loop may be formed from a shape memory material. In specific embodiments, the distal end opening may be oriented substantially perpendicular to the tubular member and oriented away from the proximal end opening. In certain embodiments, flexible material may be a solid material, and in some embodiments the flexible material may be a mesh material. In specific embodiments, the flexible material may be a polyethylene material. In particular embodiments, the pouch may comprise a generally cylindrical portion near the distal end opening. In some embodiments, the flexible pouch may comprise a tapered portion coupled to the generally cylindrical portion, and in particular embodiments may comprise an elongated portion coupled to the tapered portion.

In certain embodiments, the elongated portion may be approximately 15 centimeters long. In some embodiments, the flexible pouch may comprise a funnel-shaped overflow portion coupled to the elongated portion. In particular embodiments, the generally cylindrical portion and the tapered portion may be formed from a polyethylene material that is approximately 0.038 mm thick and the elongated portion and the funnel-shaped overflow portion may be formed from a polyethylene material that is approximately 0.051 mm thick. In some embodiments, the elongated portion may be approximately 9 mm in diameter.

Specific embodiments include a method of fragmenting a calculus in a patient, where the method may comprise: inserting a first medical device and a second medical device into the patient, where the first medical device comprises a tubular member coupled to a flexible pouch; the tubular member comprises a proximal end and a distal end; the flexible pouch comprises a distal end opening and a proximal end opening; and the second medical device is received within the flexible pouch of the first medical device via the proximal end opening. Certain embodiments may also comprise receiving the calculus into the flexible pouch through the distal end opening; manipulating the distal end opening from an open position to a closed position; and fragmenting the calculus with the second medical device.

In particular embodiments, manipulating the distal end opening from an open position to a closed position may comprise moving a control line in a direction away from the distal end of the tubular member and toward the proximal end of the tubular member. In certain embodiments, moving the control line in the direction away from the distal end of the tubular member and toward the proximal end of the tubular member causes a resilient loop extending around the distal end opening to decrease in diameter. In specific embodiments, the distal end opening may be at least 1 cm in diameter in the open position and less than 1.0 mm in diameter in the closed position. In some embodiments, the distal end opening may be at least 1 cm in diameter in the open position and less than 0.5 mm in diameter in the closed position.

In particular embodiments, inserting the first medical device into the patient may comprise inserting the first medical device into a kidney. In some embodiments, inserting the first medical device into the patient may comprise inserting the first medical device into a urinary bladder. In certain embodiments, inserting the first medical device into the patient may comprise inserting the first medical device into a urethra. In some embodiments, inserting the first medical device into the patient may comprise inserting the first medical device into a ureter, nasal passage, gastrointestinal tract, or salivary gland. In specific embodiments, inserting the first medical device into the patient may comprise inserting the first medical device through an access sheath or cannula. In some embodiments, the second medical device may be a lithotripsy device. In certain embodiments, fragmenting the calculus with the second medical device may comprise delivering a chemical to the calculus.

In specific embodiments, fragmenting the calculus with the second medical device may comprise emitting an acoustic wave from the second medical device. In certain embodiments, the second medical device may comprise a laser configured to fragment the calculus.

In particular embodiments, the second medical device may be an electrohydraulic lithotripsy device. Specific embodiments may further comprise vacuuming fragments of the calculus from the flexible pouch. Certain embodiments may further comprise removing the second medical device from the flexible pouch and withdrawing the first medical device from the patient.

Any embodiment discussed with respect to one aspect of the invention applies to other aspects of the invention as well.

The embodiments in the one section of this disclosure are understood to be embodiments of the invention that are applicable to all aspects of the invention, including those in other sections of the disclosure.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The terms "substantially" and "generally" are defined as largely but not necessarily wholly what is specified (and includes what is specified; e.g., substantially 90 degrees includes 90 degrees and generally parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, a device for removal of calculus, or a component of such a device, that is configured in a certain way is configured in at least that way, but it can also be configured in other ways than those specifically described.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Devices and methods for removal of kidney stones are disclosed herein. It should be noted, however, that while the devices and methods of the present disclosure will be described in connection with removal of kidney stones, the devices and methods of the present disclosure may be used to remove other types of stones or tissues, including, but not limited to, stone removal from ureters, urinary bladder, urethra, nasal passages, gastrointestinal track, salivary glands, or similar unwanted articles (or excised tissues) from other compartments, vessels or cavities of the body.

Figure 1:
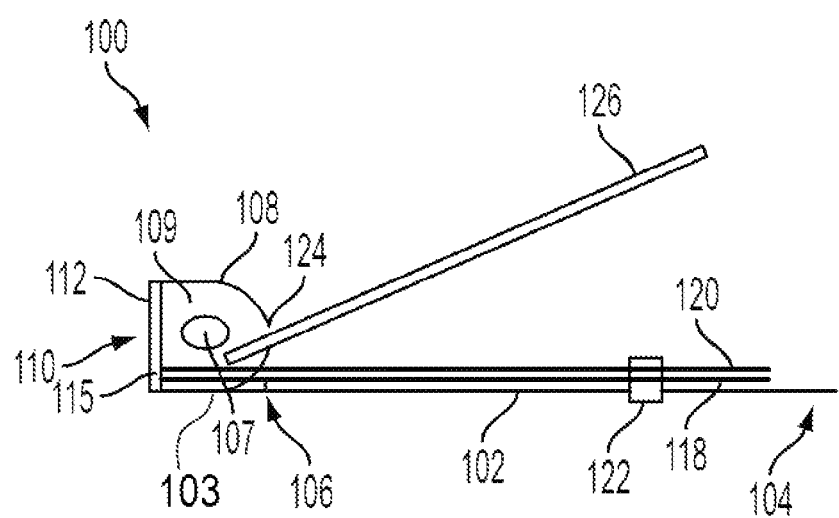
FIG. 1 shows a schematic diagram of an embodiment of a device for kidney stone removal of the present disclosure.

In reference to FIG. 1, a device 100 for removal of kidney stones of the present disclosure includes a rigid tubular member 102, having a proximal end 104 and a distal end 106. Rigid tubular member 102 may be made of any biocompatible material that provides the rigid tubular member 102 with sufficient structural integrity for advancement and withdrawal of the device in the kidney. For example, rigid tubular member 102 may be made of a biocompatible metal or metal alloy, such as, stainless steel or nitinol (or a plastic). Rigid tubular member 102 may be sized and shaped to pass into the kidney. In some embodiments, rigid tubular member 102 is designed to be inserted into the kidney through an Amplatz sheath, a cannula or a similar surgical device. In some embodiments, rigid tubular member 102 is a tube having one or more inner lumens. In exemplary embodiments, rigid tubular member 102 has a length sufficient so that in operation the proximal end 104 of rigid tubular member 102 remains outside the body of the patient. Optionally, a handle may engage at proximal end 104 of rigid tubular member 102 to assist in guiding device 100 into the body of the patient, and ultimately into the kidney.

In the embodiment shown, device 100 further comprises a flexible tubular member 103 coupled to the distal end 106 of rigid tubular member 102. In certain embodiments, flexible tubular member 103 may be a polyurethane tubular member. In a specific embodiment, flexible tubular member 103 may have an outside diameter of approximately 2 mm, an inside diameter of approximately 1 mm, and a length of approximately 15 mm. It is understood that other exemplary embodiments may comprise a tubular member with different dimensions.

Device 100 further includes a flexible pouch 108 or bag coupled to rigid tubular member 102 and flexible tubular member 103. Flexible pouch 108 defines an interior cavity 109 for receiving a kidney stone 107. Pouch 108 is sized and shaped to receive kidney stone 107 to be removed in interior cavity 109. Pouch 108 is moveable from a collapsed state for delivering pouch 108 to the kidney to a partially or completely expanded state for receiving the kidney stone. Pouch 108 can be made of a material with properties that allows the pouch 108 to be moved from a collapsed state to an expanded state. Additionally, suitable materials for pouch 108 are biocompatible, and are able to withstand exposure to various materials depending on the intended use of the device. For example, depending on the intended use, the pouch material may be exposed to materials such as acids, bases, salts, gases, solvents, etc., and/or various forms of energy such as mechanical energy, acoustic energy, laser energy, etc. Other conditions that may be taken into account in choosing a material for the flexible sheet of pouch 108 include the intended service life of the device, whether pouch 108 is to be used with a lithotripsy device, the type(s) of lithotripsy device with which it is intended to be used, etc. In general, a variety of material could be used including ceramics, polymers, polypropylene, polyethylene, metals, carbon fibers/composites, etc. In some embodiments, pouch 108 may be made from 0.038 millimeters thick clear polyethylene.

Pouch 108 has a distal end mouth or opening 110 to allow access to the interior cavity of the pouch 108. In some embodiments, distal end opening 110 is disposed on a distal face 112 of pouch 108. Distal end opening 110 located on distal face 112 of pouch 108 also provides a viewing scope with an unobstructed view to the outside of pouch 108, because the scope is aligned with distal end opening 110 so both distal end opening 110 and a stone to be removed can be seen.

Yet another potential advantage is that the mouth at the distal end also allows for direct in-line access of semi-rigid conventional grasper instruments to assist in capturing the stone inside the pouch. Distal end opening 110 may have any shape that allows the kidney stone to pass therethrough into the pouch 108. In certain embodiments, distal end opening 110 may have circular, oval, elliptical, rounded, square, or irregular shapes. Distal end opening 110 is moveable between an open configuration to allow a kidney stone to pass into the pouch 108 and a closed configuration to close or seal pouch 108. In some embodiments, distal end opening 110 has a diameter between about 20 mm and about 50 mm when in the open configuration. In some embodiments, distal end opening 110 has a diameter of about 32 mm when in the open configuration.

In some embodiments, when distal end opening 110 is in the closed configuration, a substantially air tight or near airtight seal is created around the mouth. This may allow pouch 108 to be inflated in order to create a working space inside the pouch. In some embodiments, the material for the pouch is selected so that the pouch is substantially impermeable such that the pouch prevents kidney stone fragments from escaping from the pouch. In some embodiments, pouch 108 is designed such that when pouch 108 is inflated with distal end opening 110 in the closed position; pouch 108 still contains kidney stone fragments inside pouch 108. In some embodiments, the pouch material is a very fine mesh. In some embodiments, the pouch material is a solid material. In some embodiments, pouch 108 is configured to contain fine grain sand particles under turbulent conditions, when pouch 108 is inflated and distal end opening 110 is in the closed configuration.

Figure 2:
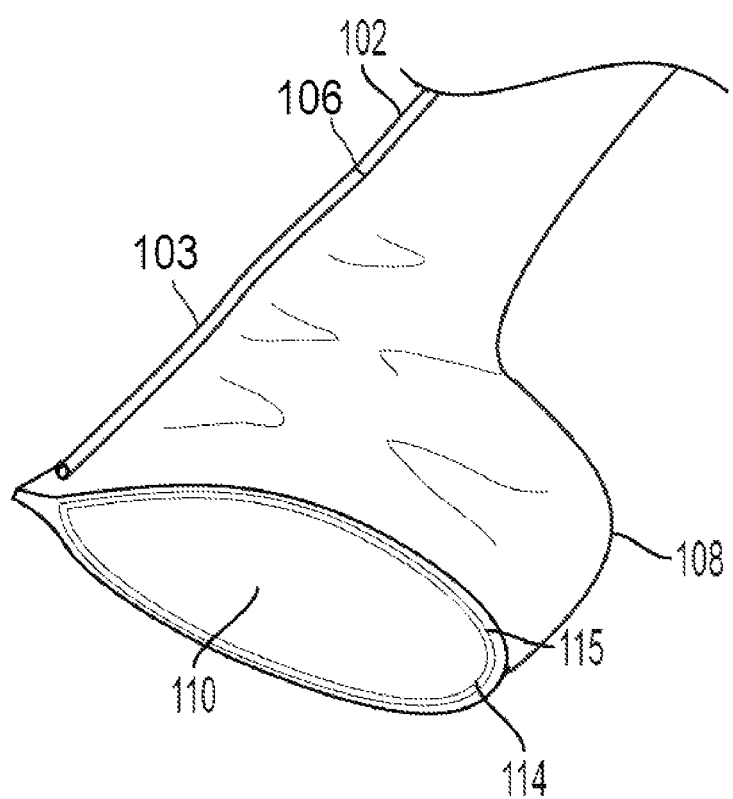
FIG. 2 shows a close-up of a pouch for capturing a kidney stone of an embodiment of a device for kidney stone removal of the present disclosure.

In reference to FIG. 2, in some embodiments, device 100 includes a resilient loop 114 disposed substantially along the perimeter of the distal end opening 110. An exterior or interior channel 115 may be provided along the perimeter of distal end opening 110 to house loop 114. In some embodiments, such channel is formed by folding the distal end of the pouch 108 over about itself to form a flap or flaps, which can then be connected to the pouch 108 by conventional means to create a channel around the distal end opening 110 for housing loop 114.

The diameter of loop 114 is changeable to allow the user to move the distal end opening 110 from the open configuration to the closed configuration, or from closed configuration to open configuration. In some embodiments, loop 114 is made from a shape memory material. Suitable shape memory materials for loop 114 include, but are not limited to, nickel-titanium, nickel-titanium-platinum, nickel-titanium-palladium, copper-aluminum-nickel, copper-zinc-aluminum, iron-manganese-silicon alloys, copper-zinc-aluminum-nickel, copper-aluminum-nickel, shape-memory polymers and similar materials. Loop 114 can be made from another material as long as the material allows loop 114 to perform the functions described herein.

Referring back to FIG. 1, in some embodiments, the ends of loop 114 are connected to loop control lines 118, 120 extending from the pouch 108 proximally toward proximal end 104 of rigid tubular member 102. In some embodiments, either the ends of loop 114 or distal ends of loop control lines 118, 120 are threaded through an opening around the bottom of the pouch 108 to connect the ends of loop 114 with loop control lines 118, 120. In some embodiments, loop control lines 118, 120 are passed through an inner lumen of rigid tubular member 102 to prevent buckling of loop control lines 118, 120, such as for example, when loop control lines 118, 120 need to be fed back into the mouth 108 to re-open it.

Loop control lines 118, 120 allow the user to adjust the diameter of loop 114, and thus the size of the distal end opening 110, by moving a free end of control lines 118, 120 in the proximal direction to reduce the diameter of loop 114 or by moving loop control lines 118, 120 in the distal direction to increase diameter of the loop 114. In some embodiments, loop 114 and loop control lines 118, 120 are integral parts of a single, continuous strand of material. In a specific embodiment, loop control lines 118, 120 and loop 114 are formed from a single nitinol wire approximately 40 inches in length.

In some embodiments, loop control lines 118, 120 may be attached to the loop by a conventional method, such as tying, welding, heat sealing, gluing and other methods known to those skilled in the art. In particular embodiments, control lines 118, 120 may be formed from nickel-titanium (also known as nitinol), nickel-titanium-platinum, nickel-titanium-palladium, copper-aluminum-nickel, copper-zinc-aluminum, iron-manganese-silicon alloys, copper-zinc-aluminum-nickel, copper-aluminum-nickel, polymer, nylon or any other biocompatible wire material.

In some embodiments, prior to insertion of device 100 into the kidney, loop 114 is deformed to reduce the profile of device 100 and allow for easier passage of device 100 into the kidney. However, when device 100 is inserted into the kidney beyond the access sheath, loop 114 can resume its default shape, which causes loop 114 to automatically assume a bigger diameter to open up pouch 108. Once a kidney stone is received in pouch 108, loop control lines 118, 120 may be pulled proximally to again seal pouch 108.

In some embodiments, device 100 may include a clamp 122 or a similar device disposed along rigid tubular member 102 to secure loop control lines 118, 120 in a desired position. Loop control lines 118, 120 may pass through clamp 122, which allows sufficient movement of loop control lines 118, 120 therethrough when clamp 122 is open. On the other hand, when clamp 122 is closed, clamp 122 secures loop control lines 118, 120 relative to rigid tubular member 102 to maintain the diameter of loop 114 and the size of distal end opening 110. In this manner, loop control lines may be pulled through clamp 122 proximally to close or seal pouch 108, and clamp 122 may be closed to prevent loop 114 from loosening and allowing pouch 108 to expand or open.

Still referring to FIG. 1, pouch 108 further includes an instrument opening 124 to allow one or more surgical instruments 126 to be passed into interior cavity 109 of the pouch 108 when distal end opening 110 is closed. In this manner, the user can manipulate the kidney stone inside the pouch 108, while ensuring that neither the kidney stone nor its fragments can escape from the pouch 108 through the distal end opening 110. In some embodiments, the instrument opening 124 is provided with an elongated portion or a neck that extends proximally from the instrument opening 124 and allows irrigation fluid to circulate down an instrument inserted into the pouch 110 and out around the instrument. In this manner, the pouch 108 does not get over pressurized during the procedure. In some embodiments, the neck provides means for fluid to escape from the kidney, thereby enabling a proper fluid balance to be maintained in the kidney and closed pouch. In some embodiments, the neck provides a path for stone fragments to flow out of the body, while ensuring that the stone fragments do not reenter the kidney.

In some embodiments, one or more surgical instruments are passed directly into the pouch 108, as shown in FIG. 1. In some embodiments, the pouch 108 and the rigid tubular member 102 may be arranged and configured such that control lines 118 and 120 are passed into the pouch 108 through the interior of the rigid tubular member 102, which in certain exemplary embodiments may have a diameter of approximately 0.027 inches. In particular exemplary embodiments, surgical instruments, including stone fragmenting devices (laser, ultrasonic, etc.) can be passed through the nephroscope, which extends through the neck of device 100.

Figure 3:
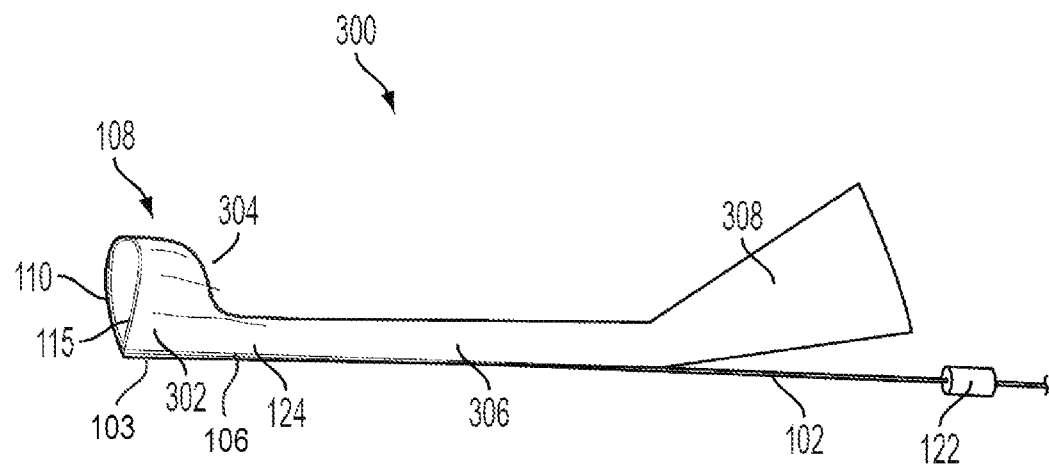
FIG. 3 shows an embodiment of a device for kidney stone removal of the present disclosure.

FIG. 3 illustrates a non-limiting embodiment of a device 300 for removal of kidney stones. The device 300 includes rigid tubular member 102 and pouch 108 coupled to flexible tubular member 103 and rigid tubular member 102, and disposed at distal end 106 of the rigid tubular member 102. In some embodiments pouch 108 comprises a distal section 302 in communication with opening 110 and a proximal section 304 that is shaped as a partial sphere or dome. It is understood that as used herein, the terms "sphere", "spherical" and "dome" are not limited a shape that is a perfect geometric sphere, but rather include a generally concave or orbicular shape. In the configuration shown, pouch 108 may slide through the access sheet more easily. Moreover, with such shape, pouch 108 may close in a round shape to aid in receiving a kidney stone inside pouch 108. In certain embodiments, pouch 108 extends approximately 40 mm from flexible tubular member 103 (e.g. when pouch 108 is an expanded state).

Pouch 108 has a distal end opening 110 and an instrument opening 124. In some embodiments, pouch 108 has an elongated portion or neck section 306 in communication with pouch 108 through instrument opening 124 and extending proximally from instrument opening 124. Elongated portion 306 may be of any size or shape as long as elongated portion 306 allows surgical instruments to be passed into pouch 108. In some embodiments, elongated portion 306 is tapered to allow unfettered passage of device 300 through the access sheath while allowing egress of irrigation fluid from pouch 108. In some embodiments, the neck has an outer diameter to fit through an access sheath, such as an Amplatz sheath and an inside diameter to accept a nephroscope. In some embodiments, elongated portion 306 has a diameter of about 5-15 mm, and in particular embodiments, about 9 mm. Elongated portion 306 provides means of fluid outflow to maintain pressure balance within the kidney. In some embodiments, the neck is provided with sufficient length to ensure that the irrigation fluid introduced through the nephroscope, which may contain kidney stone fragments, is able to backflow and egress from the kidney and pouch 108 so that pressure does not build up in the kidney or pouch 108. In some embodiments, elongated portion 306 is about 5-20 cm long, and in particular embodiments about 11 cm or 17.5 cm long. In certain embodiments configured for use with an utereroscope, elongated portion may be longer, including for example 60 cm long. In some embodiments, elongated portion 306 terminates at its proximal end in an overflow portion 308 to allow for egress of irrigation fluid. In some embodiments, overflow portion 308 is funnel-shaped.

Figure 4:
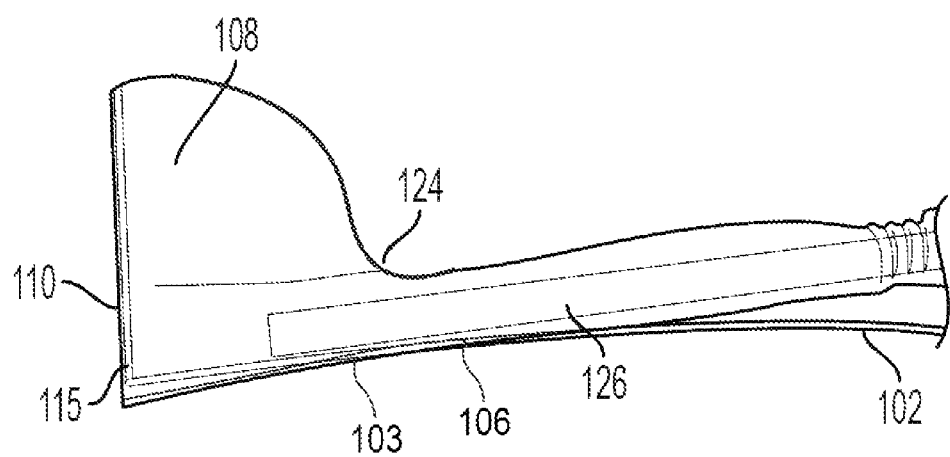
FIG. 4, FIG. 5 and FIG. 6 show an embodiment device for kidney stone removal of the present disclosure in operation.
Figure 5:
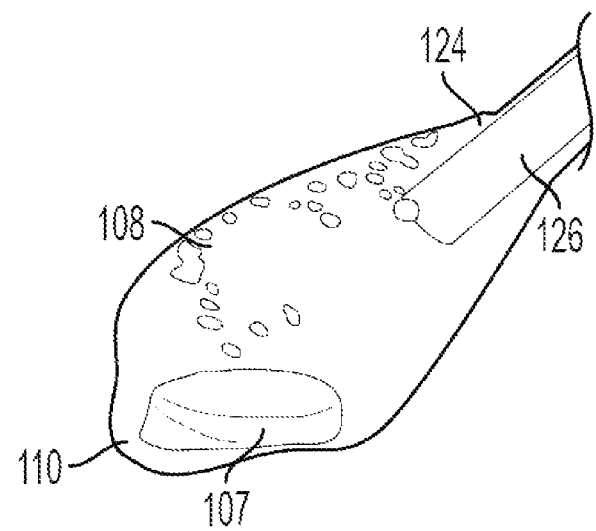

In operation, after gaining percutaneous access to the kidney, device 100 may be advanced with a nephroscope 126 through an access sheath into the kidney. Pouch 108 can be advanced through the access sheath in a collapsed state and allowed to transform to an expanded state in the kidney. As shown in FIG. 4, nephroscope 126 may be inserted into pouch 108 of device 100 through the instrument opening 124 and placed near the distal end opening 110 of pouch 108 to visualize a kidney stone 107 to be removed. Once the location of kidney stone 107 to be removed is identified, device 100, kidney stone 107 or both are manipulated to capture the kidney stone inside pouch 108 of device 100. Loop 114 may then be reduced in diameter around distal end opening 110 to close distal end opening 110 and to effectively seal pouch 108 with kidney stone 107 inside pouch 108, as shown in FIG. 5. In particular embodiments, distal end opening 110 can be substantially sealed so that interior cavity 109 is generally air and/or water tight.

If the kidney stone is too large to fit through the access sheath, the kidney stone may be fragmented by a conventional method known to those skilled in the art, including, but not limited, to by laser or mechanical fracturing. In some embodiments, the kidney stone may be fragmented using a surgical instrument 126, including for example a lithotripsy device such as a mechanical device, a device to deliver a chemical to the calculus, an acoustic device, a laser device, an electrohydraulic lithotripsy device, etc. Exemplary embodiments of such devices include the Lumenis/Coherent VersaPulse Select Holmium:YAG laser device; the ACMI CyberWand ultrasonic device, and the Storz Calcutript Electrohydraulic Lithotripter.

Figure 6:
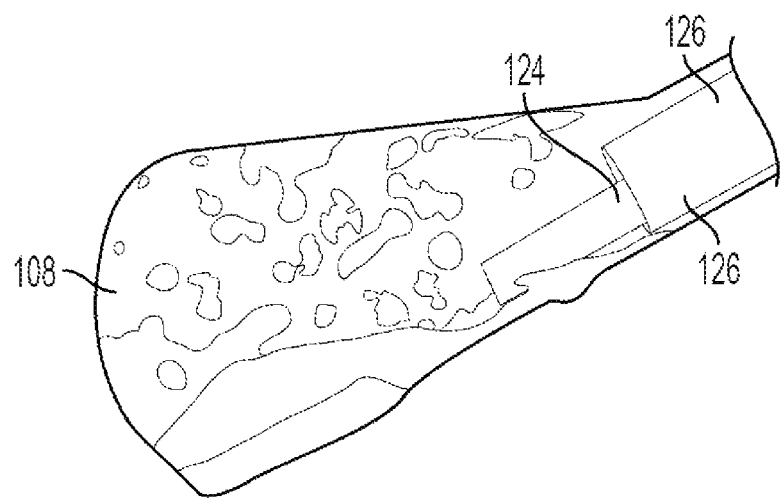

In some embodiments, an ultrasonic lithotripter with suction may be introduced into the pouch through the nephroscope to fragment and, subsequently, remove kidney stone fragments from pouch 108. As shown in FIG. 6, because distal end opening 110 of pouch 108 is sealed using loop 114, even very small kidney stone fragments produced by fragmenting the kidney stone 107 are contained within pouch 108. In particular embodiments, pouch 108 can retain a particle having a diameter of approximately 0.5 mm in diameter. These fragments may be suctioned out from the pouch or removed in another standard manner. Once all kidney stone fragments are removed from pouch 108, pouch 108 may be contracted into a collapsed state, and surgical instrument 126 and device 100 may be removed through the access sheath from the body of the patient.

In some embodiments, a device for removal of kidney stones includes a substantially sealable pouch that can be inserted through an Amplatz sheath ahead of a rigid nephroscope to entrap stones that are too large to be extracted through the sheath. Exemplary embodiments of nephroscopes suitable for use include those manufactured by Karl Storz, Olympus, Wolf and Stryker. Pouch 108 is designed to permit the surgeon to insert a fragmenting device into the pouch and fragment the stone inside the pouch. In some embodiments, stones up to 3 cm in diameter can be entrapped in the pouch and fragmented via the nephroscope and lithotrite, which can be inserted into the pouch with the kidney stone, thereby preventing stone fragments from migrating down the ureter or elsewhere within the renal collecting system. As a result, the likelihood of dispersing stone fragments during fragmentation of a large stone is greatly reduced, if not completely prevented.

In some embodiments, a method for removal of kidney stones comprises advancing a sealable pouch into the kidney, moving the pouch over a kidney stone to capture the kidney stone inside the pouch, closing a mouth of the pouch to seal the pouch, fragmenting the kidney stone into smaller fragments and removing the kidney stone fragments from the pouch while maintaining the seal of the pouch.

Results

Results using exemplary embodiments have previously been disclosed in a percutaneous cystolithopaxy model. The efficiency of stone fragmentation with and without the use of disclosed exemplary embodiments are provided below in a PCNL model.

An in-vitro PCNL model consisting of a human kidney model was created on a 3-D printer with an open upper pole calyx, renal pelvis, and ureter. A 30F Amplatz working sheath was placed in the upper pole calyx. Ten Bego® stones made in spherical molds of 2.0 cm diameter, matched for weight, were fragmented using a 24F rigid nephroscope and an ultrasonic lithotripter; five with an exemplary embodiment as disclosed herein (referred to as PercSac for purposes of discussion) and then five without the use of the PercSac. The time for stone fragmentation with ultrasonic lithotripter, total time for stone clearance from the kidney, a gross assessment of the stone-free status, and need for flexible nephroscope to achieve stone-free status were recorded.

The mean stone weight for both groups was 4.76 g (with PercSac the standard deviation was 0.12; without PercSac the standard deviation was 0.16). The median time for stone fragmentation with the ultrasonic lithotripter was significantly shorter in the PercSac group compared with the control group [217 sec (IQR=169-255) versus 340 sec (IQR=310-356), (p=0.028)]. Likewise, the total time from insertion of the nephroscope into the kidney to completion of stone clearance from the kidney was significantly shorter for the PercSac group [293 sec (IQR=244-347) versus 376 sec (IQR=375-480), p=0.047)].

One trial with the PercSac had residual dust remaining in the kidney while all five trials without the PercSac had small residual fragments remaining. All trials without the PercSac required a flexible scope with basket extraction to achieve stone-free status and none of the trials with the PercSac required flexible nephroscopy for stone clearance.

In conclusion, ultrasonic lithotripsy using the PercSac device is more efficient and efficacious than traditional ultrasonic lithotripsy in a PCNL model. This advantage may be even more pronounced during clinical PCNL where residual fragments migrate into difficult-to-access calyces.

All patents, patent applications, and published references cited herein are hereby incorporated by reference in their entirety. While the devices and methods of the present disclosure have been described in connection with the specific embodiments thereof, it will be understood that they are capable of further modification. Furthermore, this application is intended to cover any variations, uses, or adaptations of the devices and methods of the present disclosure, including such departures from the present disclosure as come within known or customary practice in the art to which the devices and methods of the present disclosure pertain.

The terms a or an, as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically. The terms about, substantially, generally, and approximately (and variations thereof) as used herein, are defined as at least approaching a given state. In specific embodiments, the terms may be defined as being largely but not necessarily wholly what is specified as understood by one of ordinary skill in the art, and in one non-limiting embodiment refers to ranges within 10%, preferably within 5%, more preferably within 1%, and most preferably within 0.5% of what is specified.

Furthermore, all the disclosed elements and features of each disclosed embodiment can be combined with, or substituted for, the disclosed elements and features of every other disclosed embodiment except where such elements or features are mutually exclusive.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

REFERENCES

The following references, to the extent that they provide exemplary procedural or other details supplementary to those set forth herein, are specifically incorporated herein by reference.

U.S. Pat. No. 4,590,938
U.S. Pat. No. 4,625,726
U.S. Pat. No. 4,893,621
U.S. Pat. No. 4,997,435
U.S. Pat. No. 5,190,542
U.S. Pat. No. 5,341,815
U.S. Pat. No. 5,403,324

U.S. Pat. No. 5,611,803
U.S. Pat. No. 6,264,663
U.S. Pat. No. 6,447,523
U.S. Pat. No. 7,537,601
U.S. Pat. No. 7,914,540
U.S. Publn. 20030178030
U.S. Publn. 20060247663

The invention claimed is:

1. A medical device for use in the removal of a calculus from a patient, the medical device comprising:
- a rigid tubular member comprising a proximal end and a distal end;
- a flexible tubular member comprising a proximal end and a distal end, wherein the proximal end of the flexible tubular member is coupled to the distal end of the rigid tubular member;
- a flexible pouch coupled to the rigid tubular member and coupled to the flexible tubular member, wherein:
  - the flexible pouch comprises a distal end opening and a proximal end opening;
  - the distal end opening is oriented substantially perpendicular to the rigid tubular member and oriented away from the proximal end of the rigid tubular member;
  - the flexible pouch is offset from the rigid tubular member;
  - wherein the flexible pouch comprises a distal portion in communication with the distal end opening;
  - the flexible pouch comprises a partial spherical portion coupled to the distal portion; and
  - the flexible pouch comprises an elongated portion coupled to the partial spherical portion;
- a resilient loop extending around the distal end opening of the flexible pouch; and
- a first control line coupled to the resilient loop, wherein the first control line is configured to manipulate the resilient loop such that the distal end opening can be moved from an open position to a closed position.

2. The medical device of claim 1 wherein the elongated portion is approximately 5-20 centimeters long.

3. The medical device of claim 1 wherein the distal end opening has a diameter of less than 1.0 mm when the distal end opening is in the closed position.

4. The medical device of claim 1 wherein the resilient loop and the first control line are formed from a single component.

5. The medical device of claim 4 wherein the resilient loop and the first control line are formed from a nitinol wire.

6. The medical device of claim 1 wherein the first control line:
- enters the proximal end of the rigid tubular member;
- exits the distal end of the flexible tubular member;
- extends through a channel around the distal end opening to form the resilient loop;
- re-enters the distal end of the flexible tubular member; and
- exits the proximal end of the rigid tubular member.

7. The medical device of claim 1 wherein the resilient loop is biased to maintain the distal end opening in the open position.

8. The medical device of claim 1 wherein the resilient loop is formed from a shape memory material.

9. The medical device of claim 1 wherein the distal end opening is between approximately 1 cm and 5 cm in diameter when the distal end opening is in the open position.

10. The medical device of claim 1 wherein:
- the first control line extends along the rigid tubular member and the flexible tubular member;
- the first control line is coupled to the resilient loop; and
- the first control line can be pulled toward the distal end of the rigid tubular member to close the distal end opening.

11. The medical device of claim 1 further comprising a second control line coupled to the resilient loop, wherein the first and second control lines are configured to manipulate the resilient loop such that the distal end opening can be closed.

12. The medical device of claim 1 wherein the resilient loop is displaced in a channel that extends around the distal end opening.

13. The medical device of claim 12 wherein the channel is formed by folding a portion of the flexible pouch.

14. A medical device for use in the removal of a calculus from a patient, the medical device comprising:
- a pouch formed from a flexible material;
- a distal end opening in the pouch;
- a proximal end opening in the pouch;
- a rigid tubular member comprising a proximal end and a distal end; and
- a flexible tubular member coupled to the pouch, wherein:
  - the pouch is offset from the rigid tubular member;
  - wherein the pouch comprises a distal portion in communication with the distal end opening;
  - the pouch comprises a partial spherical portion coupled to the distal portion; and
  - the pouch comprises an elongated portion coupled to the partial spherical portion;
  - the flexible tubular member comprises a proximal end coupled to the distal end of the rigid tubular member;
  - the distal end opening is configured to move from an open position to a closed position;
  - the distal end opening is configured to receive the calculus in the pouch when the distal end opening is in the open position;
  - the distal opening is configured to retain the calculus in the pouch when the distal opening is in the closed position; and
  - the proximal end opening is configured to receive a medical instrument configured to fragment a calculus.

15. The medical device of claim 14 wherein the distal end opening is between approximately 2 cm and 5 cm in diameter when the distal end opening is in the open position.

16. The medical device of claim 14 further comprising a control line configured to move the distal end opening from the open position to the closed position, wherein the control line extends from the distal end opening to the proximal end opening.

17. The medical device of claim 16 wherein the control line is coupled to a resilient loop extending around the distal end opening.

18. The medical device of claim 17 wherein the control line and the resilient loop are formed from a single component.

19. The medical device of claim 17 wherein the resilient loop is biased to maintain the distal end opening in the open position.

20. The medical device of claim 17 wherein the resilient loop is formed from a shape memory material.

21. The medical device of claim 14 wherein the distal end opening is oriented substantially perpendicular to the flexible tubular member and oriented away from the proximal end opening.

22. The medical device of claim 14 wherein the elongated portion is approximately 15 centimeters long.

* * * * *